(12) United States Patent
Tu et al.

(10) Patent No.: US 11,635,419 B2
(45) Date of Patent: Apr. 25, 2023

(54) PAAS PLATFORM-BASED ULTRA-LOW POWER CONSUMPTION SOIL NEAR-GROUND WIRELESS SENSING SYSTEM

(71) Applicant: INSTITUTE OF SOIL SCIENCE, CHINESE ACADEMY OF SCIENCES, Nanjing (CN)

(72) Inventors: Yonghui Tu, Nanjing (CN); Haoye Tang, Nanjing (CN); Wenyou Hu, Nanjing (CN); Chanjuan Sun, Nanjing (CN)

(73) Assignee: INSTITUTE OF SOIL SCIENCE, CHINESE ACADEMY OF SCIENCES, Nanjing (CN)

( * ) Notice: Subject to any disclaimer, the term of this patent is extended or adjusted under 35 U.S.C. 154(b) by 8 days.

(21) Appl. No.: 17/310,590

(22) PCT Filed: Aug. 26, 2019

(86) PCT No.: PCT/CN2019/102643
§ 371 (c)(1),
(2) Date: Aug. 12, 2021

(87) PCT Pub. No.: WO2020/206908
PCT Pub. Date: Oct. 15, 2020

(65) Prior Publication Data
US 2022/0107300 A1 Apr. 7, 2022

(30) Foreign Application Priority Data

Apr. 12, 2019 (CN) .......................... 201910294575.1

(51) Int. Cl.
*G01N 33/24* (2006.01)
*G01W 1/14* (2006.01)

(52) U.S. Cl.
CPC ............ *G01N 33/246* (2013.01); *G01W 1/14* (2013.01)

(58) Field of Classification Search
CPC .............................. G01N 33/246; G01W 1/14
USPC ............................................................ 702/3
See application file for complete search history.

(56) References Cited

U.S. PATENT DOCUMENTS

| 10,383,126 | B2* | 8/2019 | Gollakota | ......... H04W 28/0221 |
| 10,728,336 | B2* | 7/2020 | Akhtar | .................... G06Q 50/01 |
| 2012/0152297 | A1* | 6/2012 | Mitchell | ................. H01L 35/30 |
|  |  |  |  | 136/205 |

(Continued)

*Primary Examiner* — Ricky Go
(74) *Attorney, Agent, or Firm* — CBM Patent Consulting, LLC

(57) ABSTRACT

A PaaS platform-based ultra-low power consumption soil near-ground wireless sensing system includes a plurality of sensors mounted in soil, a signal transceiver module is arranged in the sensor, the signal transceiver module transmits a signal to a LoRaWan gateway through LoRa wireless communication, and the LoRaWan gateway is successively connected to a PaaS platform and a user group; and the sensors include a soil moisture sensor, a soil salinity sensor and a rainfall sensor. The PaaS platform-based ultra-low power consumption soil near-ground wireless sensing system of the invention enables sensor nodes to have ultra-low power consumption; and through fusion with a LoRa communication technology, a node network with ultra-low power consumption and long-distance transmission is constructed.

4 Claims, 2 Drawing Sheets

(56) References Cited

U.S. PATENT DOCUMENTS

| | | | |
|---|---|---|---|
| 2015/0351337 A1* | 12/2015 | Sabadin | F16K 31/042 |
| | | | 700/282 |
| 2017/0346953 A1* | 11/2017 | Abassi | H04M 11/007 |
| 2018/0368339 A1* | 12/2018 | van der Lee | A01G 25/167 |
| 2019/0159412 A1* | 5/2019 | Guidish | A01G 25/167 |
| 2020/0022322 A1* | 1/2020 | Lafian | H04L 9/3226 |

* cited by examiner

PAAS PLATFORM-BASED ULTRA-LOW POWER CONSUMPTION SOIL NEAR-GROUND WIRELESS SENSING SYSTEM

TECHNICAL FIELD

The present invention relates to a PaaS platform-based ultra-low power consumption soil near-ground wireless sensing system and a using method thereof, and belongs to the field of soil monitoring.

BACKGROUND

With the development of modern sensor technologies and communication technologies, data acquisition devices and systems based on various soil near-ground sensors are widely applied to acquire various physical and chemical parameters of field soil. These devices or systems are usually deployed in a field environment, and have the disadvantages of tedious wiring, high running cost, and inconvenient mounting and maintenance in practical application. In addition, a sensor network is complex in structure in a case of networking on a large scale at a regional scale, and energy consumption of nodes is high, so that it is impossible to support long-time field work through battery power supplying, thus being inconvenient for construction and application deployment of long-distance mass connection.

For example, in some soil moisture content monitoring systems, communication interface modes such as 485 or SDI-12 are used in sensor nodes, sensors are connected to a data acquisition module through cables, and then the data acquisition module realizes long-distance communication through a mobile communication network (GPRS, 3G or 4G). This networking mode is suitable for a situation that the sensors are sparsely arranged and a monitoring area is small. If a large number of sensor nodes need to be arranged in a wider field space, this networking mode will have the disadvantages of tedious wiring, high running cost, and inconvenient mounting and maintenance.

In some field and greenhouse experiments, Zigbee or Bluetooth, WIFI and other common short-distance wireless communication modes are used at a sensor end to connect to a gateway first, and then connected to the Internet through mobile communication or directly, which can reduce a network running cost to a certain extent and facilitate the deployment of more sensor nodes. However, the application of this combined communication strategy can undoubtedly increase a complexity of the sensor network, which is not conducive to the construction and application deployment of a large-scale wireless sensor network. Moreover, the increase of the sensor nodes is limited, and energy consumption also makes it difficult to support long-time field work through battery power supplying. In recent years, LPWAN (Low Power Wide Area Network) technologies represented by LoRa and NB-IoT have developed rapidly. Compared with existing wireless technologies such as Wi-Fi, Bluetooth and ZigBee, the LPWAN technologies have the advantages of ultra-low power consumption, long-distance transmission, long-time battery (two AA batteries) power supplying, low cost and large coverage capacity, so that the LPWAN technologies are increasingly applied to wireless data communication of sensor devices, especially a soil near-ground sensor.

As an emerging technology, LoRa is generally favored in market, and various manufacturers, research institutes and other units are striving for studying the technology, participating in standard formulation and setting up commercial pilots. However, there are some practical problems in application at present, this communication technology is simply subject to application combination with the sensor device only, and is not really subject to system integration with the sensor device from a bottom layer. The communication module is often independent of the sensor device, the power consumption of the communication module may satisfy the battery power supplying, but the sensor device is still based on a traditional application design, the power consumption cannot satisfy long-time battery power supplying, and the sensor device is still powered by commercial power or solar energy, which is inconvenient in application deployment and requires a lot of maintenance work, so that the advantages of the LoRa technology are not really showed. A self-constructed sensor system based on private cloud also has high costs in design, mounting, deployment and upgrade, which cannot satisfy more and more sensor connection demands, and data and device management demands for multiple applications.

Therefore, aiming at a large number of existing soil near-ground sensor devices based on the traditional application design, a way to apply the LoRa technology, give full play to the advantages of ultra-low power consumption, long-distance transmission, long-time battery power supplying, low cost and large coverage capacity, and construct a wireless sensor system with characteristics of mass connection, data storage and device management has important practical significance and economic value.

SUMMARY

Objective of the invention: in order to overcome the defects in the prior art, the present invention provides a PaaS platform-based ultra-low power consumption soil near-ground wireless sensing system and a using method thereof to enable sensor nodes to have ultra-low power consumption, so that maintaining the nodes to work for a long time through single power supplying of a single battery is satisfied; and through fusion with a LoRa communication technology, a node network with ultra-low power consumption and long-distance transmission is constructed, and economic values of existing sensors are fully achieved.

Technical solutions: in order to solve the above technical problems, a PaaS platform-based ultra-low power consumption soil near-ground wireless sensing system of the present invention includes a plurality of sensors mounted in soil, wherein a signal transceiver module is arranged in the sensor, the signal transceiver module transmits a signal to a LoRaWan gateway through LoRa wireless communication, and the LoRaWan gateway is successively connected to a PaaS platform and a user group; and the sensors include a soil moisture sensor, a soil salinity sensor and a rainfall sensor, and real-time data of the rainfall sensor is used as a parameter for calculating a sampling period T of the soil moisture sensor.

Preferably, the sensor is connected to a ternary lithium battery through a voltage boosting device, the ternary lithium battery is connected to the signal transceiver module through a voltage reducing device, and a controller is connected between the sensor and the signal transceiver module.

Preferably, the sampling period of the soil moisture sensor is consistent with a sampling period of the soil salinity sensor, the sampling period of the soil moisture sensor is $$T(n+1) - T(n) * \frac{\Delta}{|\theta(n) - \theta(n-1)|} * 1/R * E_0,$$

T(n) is an $n^{th}$ sampling period of the soil moisture sensor, $\theta(n)$ is a soil moisture value acquired by the sensor, $\Delta$ is a maximum allowable deviation of two data before and after maintaining a data integrity, R is a rainfall grade, and $E_0$ is an empirical parameter, wherein R is real-time weather forecast data, R is obtained by measured rainfall of the rainfall sensor, and values of R are 1, 2, 3, 4, 5, 6 and 7, which are sequentially increased, and respectively represent no rain, light rain, moderate rain, heavy rain, excessive rain, torrential rain and extraordinary rain, and $E_0$ serves as an empirical parameter, which is capable of adjusting the sampling period to a suitable value at an initial stage according to actual application requirements, for example, an initial sampling period T0 is set, and in a case of artificial irrigation, the initial sampling period T0 may be corrected in real time.

Preferably, a wireless charging coil is arranged outside the ternary lithium battery, and a casing is sheathed outside the wireless charging coil.

A using method of the PaaS platform-based ultra-low power consumption soil near-ground wireless sensing system includes the following steps of:

(1) distributing the soil moisture sensor, the soil salinity sensor and the rainfall sensor in a study area, and debugging the whole wireless sensing system;

(2) setting a maximum allowable deviation $\Delta$ and an initial sampling period T(0) of the sensor;

(3) transmitting sensor data to the PaaS platform through a LoRa communication module, and storing the sensor data by the PaaS platform; and (4) calculating a deviation M of two adjacent sampling data, and calculating a sampling period according to a formula $$T(n+1) - T(n) * \frac{\Delta}{|\theta(n) - \theta(n-1)|} * 1/R * E_0.$$

In the present invention, a power supply battery is connected to the wireless charging coil and may be charged wirelessly, so that a node battery may be charged wirelessly after running out of battery power, thus reusing the node, and moreover, according to the wireless charging design, it is unnecessary to reserve a charging interface or a detachable battery structure on node hardware, so that the sensor nodes are more compact as a whole, satisfy integrated packaging, and are more convenient to maintain. The sensor nodes are integrally packaged with black flame-retardant epoxy resin, and are integrally formed with a customized stainless steel mold, with a high mechanical strength, a heat resistance, a water resistance and a corrosion resistance, thus being really easy for large-scale deployment and maintenance-free.

In the present invention, the LoRa gateway is designed based on a SX1301 transceiver controller of Semtech company, and integrates a LTEDTU function. The LoRa gateway is powered by solar energy, and due to a large coverage radius of a network of the LoRa gateway and a strong connection load capacity (up to 10,000 terminals), large-scale networking may be carried out by a single LoRa gateway, and the large-scale networking may be satisfied by a set of solar power supply system, thus making application deployment more convenient.

An open internet of things platform OneNet at a carrier level is used as a PaaS cloud computing platform to build an efficient, stable and safe application platform between a user application and a sensor device. In a case of being device-oriented, the application platform is adaptable to various network environments and common transmission protocols, and a sensor terminal device may be accessed quickly. In a case of being user application-oriented, the application platform provides abundant API and data distribution capabilities to satisfy development requirements of various application systems. An application satisfying multiple scenario requirements is realized by using abundant graph display assemblies. In the present invention, the sensor nodes access to the PaaS platform through TCP passthrough communication, a protocol is defined by a user, and protocol analysis is finished by uploading an analysis script. In the present invention, a protocol analysis script is written with a lua script language, which includes regularly issuing a data task initialization function "device_timer_init(dev)" and analyzing data uploaded by the device "device_data_analyze".

In the present invention, 12 V direct current power supply is generally used, and chips including a node MCU, a flash chip, a RS485 transceiver, and the like are powered at 3.3 V, so that a battery voltage is boosted to 12 V in a circuit hardware structure to supply power for the sensors, on the other hand, the chips are powered at stable 3.3 V outputted by multiple linear voltage regulators, the node hardware system realizes global power supplying of a single battery, which simplifies a hardware structure and is convenient for application deployment. The chips of the nodes are selected based on low power consumption, and the sensors have a high working voltage and a large current which can reach 100 mA to 250 mA, thus being a main energy consumption part of the whole nodes; while on the other hand, in practical application, the soil near-ground sensor does not need to acquired data continuously for a long time, and will be idle for most of the time in a data acquisition and transmission period. Therefore, a sensor with enable control is designed to be powered at 12 V in the aspect of node hardware. Once the system detects that the sensor works and outputs data effectively, a boosting chip is immediately controlled to stop working, and the power supply of the sensor is cut off, thus avoiding continuous power consumption of the sensor when the node is idle. In addition, the sensor nodes may also receive external commands, for example, receive the commands from the user application platform to modify parameter settings of the nodes, and according to actual requirements, a data acquisition period of the sensors may be flexibly changed, and a total working time of the sensors can be reduced while ensuring a validity and an integrity of data, thus prolonging a field working time of a sensor battery.

In addition, a channel detection technology (CAD) of LoRa may also be used to wake up the nodes in air to work, so that working modes of the sensor nodes are flexible and satisfy multiple application scenario requirements. The series of designs will greatly reduce overall power consumption of the nodes in practical application, and make it possible to maintain the nodes to work for a long time by single power supplying of a single battery. A client may wake up the nodes in air by the channel detection technology (CAD) of LoRa to modify the sampling period; or the sensors modify the sampling periods of the sensors in a case of waking up periodically, which start to be executed in next sampling period. In one period, the sensors continuously acquire data for three times, take an arithmetic mean value as current sampling value, and transmit the sampling value through the LoRa module, and then the sensor nodes immediately enter a sleep mode and wake up automatically when the next sampling period starts. If a single sampling time of the sensor is Δt, then the sampling period should satisfy T>=3Δt.

In the present invention, the rainfall sensor does not need to be set with a fixed sampling period, the rainfall sensor is waked up in real time through external interruption in a case of rainfall to enter a sampling working state, and enters a sleep state in a case of no rainfall. A tipping bucket-type rainfall sensor is used as the rainfall sensor, and a metering assembly is a tipping bucket-type mechanical bistable weighing mechanism, which plays a role of converting a rainfall depth in mm into a switch signal to be outputted. A tipping bucket is molded by injection with engineering plastics and divided into two half cone chambers with an equal volume by a middle division plate. The tipping bucket is a mechanical bistable structure, and when one chamber receives water, the other chamber is in a waiting state. When a volume of rainwater received reaches a preset value of 0.2 mm, the tipping bucket is turned over due to the action of gravity and is in a waiting state, while the other chamber is in a water receiving working state. When the volume of rainwater received reaches the preset value, the tipping bucket is turned over again and is in a waiting state. Magnetic steel is mounted on a side wall of the tipping bucket, which scans from a side of a dry reed pipe when the magnetic steel is turned over with the tipping bucket, so as to make the dry reed pipe on and off. That is to say, every time the tipping bucket is turned over, the dry reed pipe is turned on once to transmit a switch signal (pulse signal). Therefore, the rain sensor is in a sleep state at ordinary times, and the pulse signal of the dry reed pipe is used as an input of external interruption to wake up the rainfall sensor from the sleep state.

In the present invention, taking the soil moisture sensor as an example, for soil of a certain area and a certain thickness, a change of a soil moisture content should be equal to a difference between an inflow term and an outflow term within a period of time. A positive value represents increase of the soil moisture content, while a negative value represents decrease of the soil moisture content. ΔW=P+I+U−ET−D−R−In, wherein ΔW refers to a change of the soil moisture content, inflow: P refers to rainfall, mm, I refers to an irrigation volume, mm, and U refers to upstream capillary water, mm, and outflow: E refers to soil surface evaporation, mm, T refers to a transpiration volume, mm, D refers to leakage volume, mm, R refers to runoff volume, mm, and In refers to canopy interception volume, mm. A simplified formula of soil moisture balance is ΔW=P+I−ET−D.

It can be seen that the soil moisture mainly comes from atmospheric precipitation and artificial irrigation water, and rise of groundwater and condensation of water vapor in atmosphere are also sources of the soil moisture. Meanwhile, due to various forces applied to moisture in soil, such as gravity, capillary attraction, water molecule attraction, and surface molecule attraction of soil particles, different types of moisture movements and moisture transformations (evaporation and transpiration) in different media are formed, and moisture migration in a soil-plant-atmosphere continuum (SPAC) also affects a final soil moisture content.

According to a basic equation of an unsaturated soil moisture movement:

$$\frac{\partial \theta}{\partial t} = \frac{\partial \left[ K(\theta) \frac{\partial \psi}{\partial x} \right]}{\partial x} + \frac{\partial \left[ K(\theta) \frac{\partial \psi}{\partial y} \right]}{\partial y} + \frac{\partial \left[ K(\theta) \frac{\partial \psi}{\partial z} \right]}{\partial z} \quad (1)$$

θ is a moisture content, t is time, K is a permeability coefficient, ψ is a total soil moisture potential of unsaturated soil, and x, y and z are coordinate axis directions. Therefore, under certain soil depth and texture, main influencing factors of the unsaturated soil moisture content are atmospheric precipitation and artificial irrigation. In a soil moisture monitoring network, acquisition of the soil moisture is a series of discrete sets, and a difference between two data before and after shows a change trend of the soil moisture. In a certain change range, the sampling period may be prolonged, thus reducing a number of times when the sensors are waked up to work; and in a case of exceeding a certain range, the sampling period needs to be shortened and the number of times of data acquisition needs to be increased to maintain a data integrity.

Beneficial effects: the PaaS platform-based ultra-low power consumption soil near-ground wireless sensing system of the present invention enables the sensor nodes to have ultra-low power consumption, so that maintaining the nodes to work for a long time through single power supplying of a single battery is satisfied; through fusion with the LoRa communication technology, the node network with ultra-low power consumption and long-distance transmission is constructed, and economic values of existing sensors are fully achieved; and the sensor nodes may receive the external commands, and transmit the commands from the user application platform to modify the parameter settings of the nodes, and according to actual application, the sampling period is adjusted proportionally, and the total working time of the sensors is reduced while ensuring a validity and an integrity of data, thus prolonging one field working time of the sensor battery.

DETAILED DESCRIPTION

The present invention is further described hereinafter with reference to the accompanying drawings.

Figure 1:
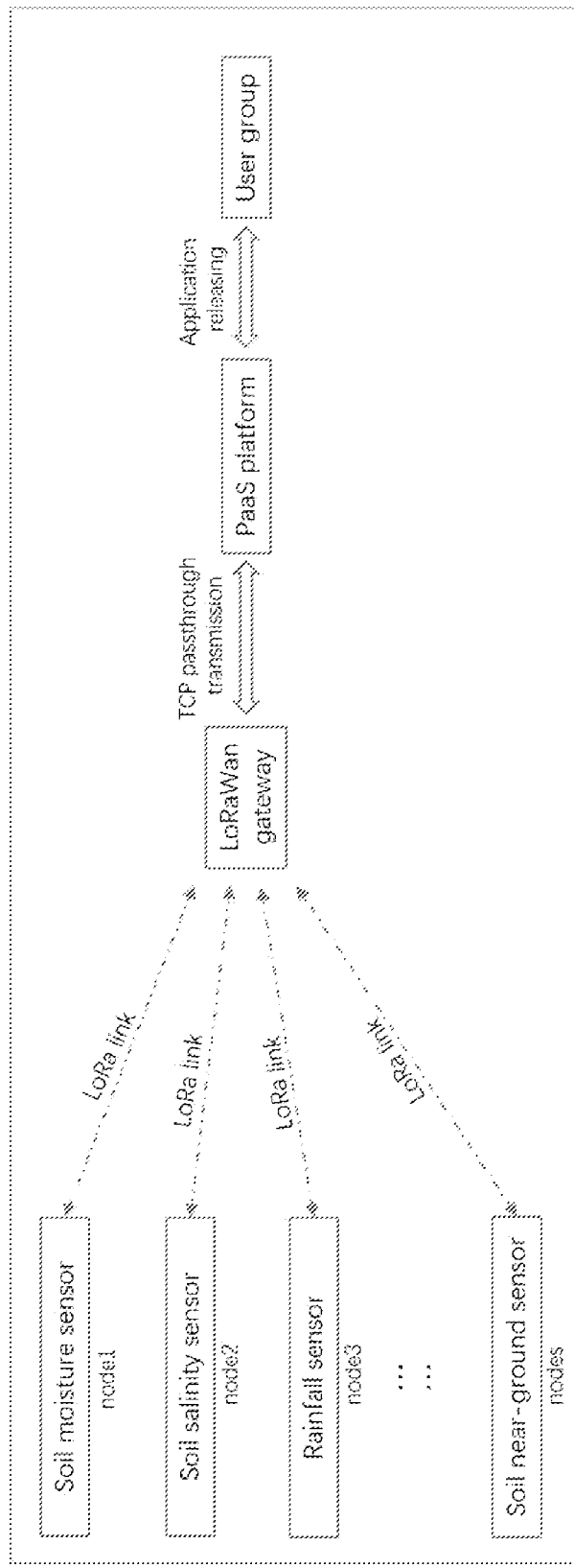
FIG. 1 is a constitutional diagram of a system of the present invention.
Figure 2:
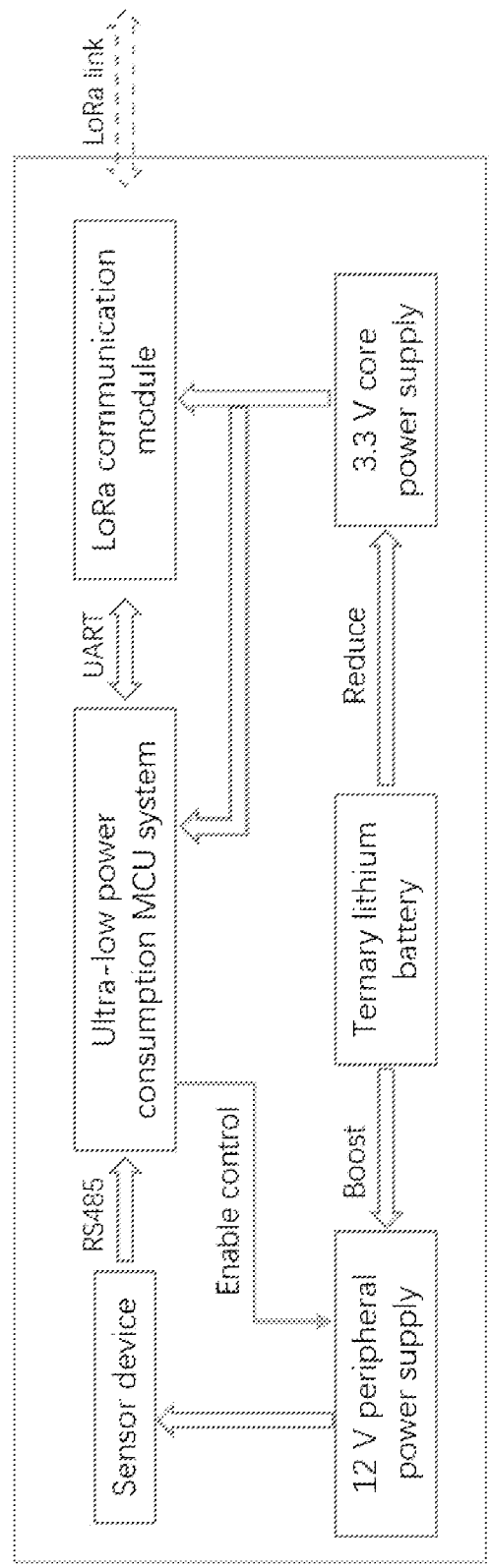
FIG. 2 is a schematic constitutional diagram of a power supply of the present invention.

As shown in FIG. 1 and FIG. 2, a PaaS platform-based ultra-low power consumption soil near-ground wireless sensing system of the present invention includes a plurality of sensors mounted in soil, wherein a signal transceiver module is arranged in the sensor, the signal transceiver module transmits a signal to a LoRaWan gateway through LoRa wireless communication, and the LoRaWan gateway is successively connected to a PaaS platform and a user group. The sensors include soil near-ground sensors such as a soil moisture sensor, a soil salinity sensor and a rainfall sensor, and real-time data of the rainfall sensor is used as parameters for calculating a sampling period T of the soil moisture sensor.

In the present invention, the sensor is connected to a ternary lithium battery through a voltage boosting device, the ternary lithium battery is connected to the signal transceiver module through a voltage reducing device, and a controller is connected between the sensor and the signal transceiver module. A wireless charging coil is arranged outside the ternary lithium battery, and a casing is sheathed outside the wireless charging coil. The sampling period of the soil moisture sensor is $$T(n+1) = T(n) * \frac{\Delta}{|\theta(n) - \theta(n-1)|} * 1/R * E_0,$$

T(n) is an $n^{th}$ sampling period of the soil moisture sensor, $\theta(n)$ is a soil moisture value acquired by the sensor, $\Delta$ is a maximum allowable deviation of two data before and after maintaining a data integrity, R is a rainfall grade, and $E_0$ is an empirical parameter. R is obtained by measured rainfall of the rainfall sensor, and values of R are 1, 2, 3, 4, 5, 6 and 7, which are sequentially increased, and respectively represent no rain, light rain, moderate rain, heavy rain, excessive rain, torrential rain and extraordinary rain, and $E_0$ serves as an empirical parameter, which is capable of adjusting the sampling period to a suitable value at an initial stage according to actual application requirements, and in a case of artificial irrigation, the initial sampling period T0 may be corrected in real time. When a difference between two data of the sensor before and after does not exceed $\Delta$, the sampling period will be gradually increased according to the formula; and when the difference exceeds $\Delta$, the sampling period will be shortened through proportional adjustment. Therefore, a total working time of the sensors can be reduced through proportional adjustment of the sampling period while ensuring a validity and an integrity of data, and a sleeping time of the sensor node is maximized, thus prolonging one field working time of a sensor battery.

A using method of the PaaS platform-based ultra-low power consumption soil near-ground wireless sensing system includes the following steps.

(1) The soil moisture sensor, the soil salinity sensor and the rainfall sensor are distributed in a study area, and the whole wireless sensing system is debugged.

(2) A maximum allowable deviation $\Delta$ and an initial sampling period T(0) of the sensor are set. In an initial stage of distribution of the sensors, the sampling period is set to be unchanged, that is, T(0)=T(1), and sampling is carried out to obtain first two sampling data $\theta(0)$ and $\theta(1)$. If there is no rainfall, R=1, and a third sampling period $$T(2) = T(1) * \frac{\Delta}{|\theta(1) - \theta(0)|} * 1/R * E_0$$

is calculated according to the formula. Calculating M=$|\theta(1)-\theta(0)|$, if M<=$\Delta$, the change of two sampling data before and after falls within an allowable range, and according to the formula, the sampling period will be increased; and if M>$\Delta$, the sampling period will be reduced. An appropriate empirical value $E_0$ is set according to experience to adjust a change speed of the sampling period.

(3) Sensor data is transmitted to the PaaS platform through a LoRa communication module, and the sensor data is stored by the PaaS platform.

(4) A deviation M of two adjacent sampling data is calculated, and a sampling period is calculated according to a formula $$T(n+1) = T(n) * \frac{\Delta}{|\theta(n) - \theta(n-1)|} * 1/R * E_0.$$

If M<=$\Delta$, the change of the two sampling data before and after falls within the allowable range, the sampling period will be increased according to the formula; and if M>$\Delta$, the sampling period will be reduced. It can be seen from the formula that the sampling period T will always be dynamically adjusted and continuously optimized to make the sensors obtain maximum sleeping time while maintaining an integrity of the sampling data, so as to satisfy a requirement of maintaining the sensor nodes to work for a long time through single power supplying of a single battery.

The above method of the present invention has many advantages, for example, 1) the ultra-low power consumption hardware structure is used in the present invention to enable the sensor nodes to have ultra-low power consumption, so that maintaining the nodes to work for a long time through single power supplying of a single battery is satisfied; and through fusion with a LoRa communication technology, a node network with ultra-low power consumption and long-distance transmission is constructed, and economic values of existing sensors are fully achieved. 2) The sensor nodes may also receive external commands, and transmit the commands from the user application platform to modify parameter settings of the nodes. According to actual application requirements, the sampling period is adjusted proportionally according to the formula, and a total working time of the sensors can be reduced while ensuring a validity and an integrity of data, thus prolonging one field working time of a sensor battery. 3) Single-battery multi-output global power supplying is used in the node of the soil near-ground sensor of the present invention, which simplifies the hardware structure without needing to be connected to commercial power or solar energy, thus avoiding cable connection during mounting, realizing real "wireless", and greatly facilitating application deployment in the field. In addition, due to a super connection load capacity of the LoRa gateway, only a few solar power supply systems need to be mounted during large-scale networking. 4) When being consumed, a node battery may be recharged wirelessly and then reused, without reserving a charging interface or a detachable battery structure, and the node battery is cured and packaged with black flame-retardant epoxy resin as a whole, with a high mechanical strength, a heat resistance, a water resistance and a corrosion resistance, thus being really maintenance-free or convenient to maintain in the later period. 5) Through development based on the PaaS platform of the operator, the soil near-ground wireless sensor system with mass connection, data storage, device management, rule engine and event warning is constructed, and an efficient, stable and safe application platform is built between a sensor device and a user. The user may also transmit instructions from the application platform to the network nodes, so that the nodes have a working mode that the period is adjustable and the nodes may be waked up in real time to satisfy multiple application scenario requirements.

Those described above are merely the preferred embodiments of the present invention, and it should be pointed out that those of ordinary skills in the art may further make improvements and decorations without departing from the principle of the present invention, and these improvements and decorations should also be regarded as the scope of protection of the present invention.

What is claimed is:

1. A PaaS platform-based ultra-low power consumption soil near-ground wireless sensing system, comprising a plurality of sensors mounted in soil, wherein a signal transceiver module is arranged in the sensor, the signal transceiver module transmits a signal to a LoRaWan gateway through a LoRa wireless communication, and the LoRaWan gateway is successively connected to a PaaS platform and a user group; and the plurality of sensors comprise a soil moisture sensor, a soil salinity sensor and a rainfall sensor; wherein a sampling period of the soil moisture sensor is $$T(n+1) = T(n) * \frac{\Delta}{|\theta(n) - \theta(n-1)|} * 1/R * E_0,$$

T(n) is an $n^{th}$ sampling period of the soil moisture sensor, θ(n) is a soil moisture value acquired by the sensor, Δ is a maximum allowable deviation of two data before and after maintaining a data integrity, R is a rainfall grade, and $E_0$ is an empirical parameter, wherein R is real-time weather forecast data, R is obtained by measured rainfall of the rainfall sensor, and values of R are 1, 2, 3, 4, 5, 6 and 7, which are sequentially increased, and respectively represent no rain, light rain, moderate rain, heavy rain, excessive rain, torrential rain and extraordinary rain, and $E_0$ serves as an empirical parameter, which is capable of adjusting the sampling period to a suitable value at an initial stage according to actual application requirements.

2. The PaaS platform-based ultra-low power consumption soil near-ground wireless sensing system according to claim 1, wherein the sensor is connected to a ternary lithium battery through a voltage boosting device, the ternary lithium battery is connected to the signal transceiver module through a voltage reducing device, and a controller is connected between the sensor and the signal transceiver module.

3. The PaaS platform-based ultra-low power consumption soil near-ground wireless sensing system according to claim 2, wherein a wireless charging coil is arranged outside the ternary lithium battery, and a casing is sheathed outside the wireless charging coil.

4. A using method of the PaaS platform-based ultra-low power consumption soil near-ground wireless sensing system according to claim 2, comprising the following steps of:
  (1) distributing the soil moisture sensor, the soil salinity sensor and the rainfall sensor in a study area, and debugging the whole wireless sensing system;
  (2) setting a maximum allowable deviation Δ and an initial sampling period T(0) of the sensor;
  (3) transmitting sensor data to the PaaS platform through a LoRa communication module, and storing the sensor data by the PaaS platform; and
  (4) calculating a deviation M of two adjacent sampling data, and calculating a sampling period according to a formula $$T(n+1) = T(n) * \frac{\Delta}{|\theta(n) - \theta(n-1)|} * 1/R * E_0.$$

* * * * *